United States Patent
Foray et al.

(10) Patent No.: US 10,180,437 B2
(45) Date of Patent: Jan. 15, 2019

(54) PREDICTIVE METHOD FOR DETERMINING TISSUAL RADIOSENSITIVITY

(71) Applicants: UNIVERSITE CLAUDE BERNARD LYON 1, Villeurbanne (FR); CENTRE NATIONAL DE LA RECHERCHE SCIENTIFIQUE, Paris (FR); CENTRE LEON BERARD, Lyons (FR); INSTITUT NATIONAL DE LA SANTÉ ET DE LA RECHERCHE MÉDICALE, Paris (FR)

(72) Inventors: Nicolas Foray, Meyrie (FR); Adeline Granzotto, Lyons (FR); Clément Devic, Lyons (FR)

(73) Assignees: UNIVERSITE CLAUDE BERNARD LYON 1, Villeurbanne (FR); CENTRE NATIONAL DE LA RECHERCHE SCIENTIFIQUE, Paris (FR); CENTRE LEON BERARD, Lyons (FR); INSTITUT NATIONAL DE LA SANTE ET DE LA RECHERCHE MEDICALE, Paris (FR)

( * ) Notice: Subject to any disclaimer, the term of this patent is extended or adjusted under 35 U.S.C. 154(b) by 0 days.

(21) Appl. No.: 15/119,664

(22) PCT Filed: Feb. 16, 2015

(86) PCT No.: PCT/FR2015/050370
§ 371 (c)(1),
(2) Date: Aug. 17, 2016

(87) PCT Pub. No.: WO2015/121597
PCT Pub. Date: Aug. 20, 2015

(65) Prior Publication Data
US 2017/0010254 A1     Jan. 12, 2017

(30) Foreign Application Priority Data

Feb. 17, 2014 (FR) ..................... 14 51215
Feb. 17, 2014 (FR) ..................... 14 51216
Oct. 10, 2014 (FR) ..................... 14 02281
Oct. 10, 2014 (FR) ..................... 14 02282

(51) Int. Cl.
*G01N 33/50* (2006.01)
*G01N 33/68* (2006.01)

(52) U.S. Cl.
CPC ..... *G01N 33/6881* (2013.01); *G01N 33/5005* (2013.01); *G01N 33/5014* (2013.01); *G01N 2333/47* (2013.01); *G01N 2333/4703* (2013.01); *G01N 2333/912* (2013.01); *G01N 2800/52* (2013.01)

(58) Field of Classification Search
CPC .................................................. G01N 33/5014
See application file for complete search history.

(56) References Cited

PUBLICATIONS

Kato et al. Radiation Research, 2006, 166:443-453.*
Charles Thomas et al., "Impact of dose-rate on the low-dose hyper-radiosensitivity and induced radioresistence (HRS/IRR) response", International Journal of Radiation Biology, vol. 89, No. 10, Oct. 1, 2013, 13 pages.
C. Colin et al., "MRE11 and H2AX biomarkers in the response to low-dose exposure: balance between individual susceptibility to radiosensitivity and to genomic instability", International Journal of Low Radiation, Inderscience Publishers, vol. 8, No. 2, Dec. 13, 2011, 11 pages.
A. Granzotto et al., "Towards a first classification of human radiosensitivity: radiotherapy, radiodiagnosis and history of radiobiology", Centre de Recherche en Cancerologie de Lyon, Mar. 30, 2012, 1 page.
Aurelie Joubert et al, "Irradiation in Presence of Iodinated Contrast Agent Results in Radiosensitization of Endothelial Cells: Consequences for Computed Tomography Therapy", International Journal of Radiation: Oncology Biology Physics, vol. 62, No. 5, Aug. 1, 2005, 11 pages, Pergamon Press, USA.
A. Joubert et al., "Intrinsic radiosensitivity and DNA double-strand breaks in human cells", Cancer Radiotherapie, vol. 11, No. 3, Feb. 23, 2007, 14 pages, Elsevier Masson, Paris, France; (English Abstract).
Charles Thomas et al., "Low-dose hyper-radiosensitivity of progressive and regressive cells isloated from a rat colon tumour: Impact of DNA repair", International Journal of Radiation Biology, vol. 84, No. 7, Jul. 1, 2008, 16 pages. Informa Healthcare, UK.
Michel Bourguignon, "Actualites en radioprotection Seuil probabiliste chez l'adulte", Feb. 10, 2012, 39 pages.
Nicolas Foray, "Les réparatoses: nouveaux concepts sur la prédiction de la radiosensibilité", Jan. 25, 2008, 37 pages.

* cited by examiner

*Primary Examiner* — Bin Shen
(74) *Attorney, Agent, or Firm* — Jordan IP Law, LLC; Todd A. Vaughn

(57) ABSTRACT

A method for predicting cellular, tissue and clinical radiosensitivity, which is based on the determination and correlation of multiple parameters and cellular and enzymatic criteria.

15 Claims, 6 Drawing Sheets ical PREDICTIVE METHOD FOR DETERMINING
TISSUAL RADIOSENSITIVITY

CROSS-REFERENCE TO RELATED
APPLICATIONS

The present application is a National Stage Application of PCT International Application No. PCT/FR2015/050370 (filed on Feb. 16, 2015), under 35 U.S.C. § 371, which claims priority to French Patent Application Nos. FR 1451215 (filed on Feb. 17, 2014), FR 1451216 (filed on Feb. 17, 2014), FR 1402282 (filed on Oct. 10, 2014), and FR 14002281 (filed on Oct. 10, 2014), which are each hereby incorporated by reference in their respective entireties.

TECHNICAL FIELD

The invention relates to the field of medical radiobiology, and more specifically the field of radiobiological laboratory methods. The invention relates to a new method for predicting cellular, tissue and clinical radiosensitivity, which is based on the determination and correlation of multiple parameters and cellular and enzymatic criteria.

BACKGROUND

Around 1 to 15% of patients treated by radiotherapy for cancer have a tissue reaction (such as dermatitis or proctitis), which may hinder the treatment insofar as it may lead the physician to decide to stop the radiotherapy treatment before the end of the planned protocol. Moreover, this tissue reaction is an indicator of a particularly high sensitivity of the patient to ionizing radiation. Thus, the radiotherapy treatment, even if interrupted upon the appearance of the first visible tissue signs, may increase morbidity or even post-treatment mortality of patients, not only because the cancer that was supposed to be treated could not be fully eradicated due to the premature discontinuation of treatment but due to collateral damage to healthy tissue caused by the radiation itself.

It is also known that the question of sensitivity of tissue to ionizing radiation is inseparable from those of DNA damage repair mechanisms. In fact, at the cellular level, ionizing radiation may break certain types of chemical bonds, producing free radicals (in particular by peroxidation) and other reactive species produced by DNA damage. DNA damage by endogenous or exogenous stress (such as ionizing radiation and free radicals), may lead to different types of DNA damage in particular according to the energy applied: base damage, single-strand breaks and double-strand breaks (DSB). Non-repaired DSBs are associated with cell death, toxicity and more specifically radiosensitivity. Poorly repaired DSBs are associated with genomic instability, mutagenic phenomena and predisposition to cancer. The organism has systems for repair specific to each type of DNA damage. Concerning DSBs, mammals have two main modes of repair: repair by suture (strand ligation) and repair by recombination (insertion of a homologous or non-homologous strand).

It is known that sensitivity of tissues to ionizing radiation is highly variable from one organ to another and from one individual to another; the idea of "intrinsic radiosensitivity" was conceptualized by Fertil and Malaise in 1981. Thus, the various studies on the therapeutic effects and the adverse effects of radiotherapy have demonstrated that there are individuals with particularly high radioresistance, and individuals who, by contrast, have radiosensitivity that may range from a clinically recognized but inconsequential adverse effect to a lethal effect. Even outside of certain rare cases of extreme radiosensitivity, the genetic origin of which appears to be recognized, it is thought that radiosensitivity is generally based on a genetic predisposition: it is therefore specific to an individual. It would therefore be desirable to have a predictive test method in order to determine the maximum cumulative dose that a given patient may receive without risk. This question is posed first in radiotherapy in a context of high ionizing doses. However, this question may also be posed for any other exposure to high ionizing doses, equivalent to those used in radiotherapy.

It is known that two proteins of the kinase family, commonly called ATM and ATR, are involved in the detection, repair and signaling of DSBs; their action requires at least the presence of a protein known as BRCA1 and an ordered cascade of phosphorylations of the different ATM substrates (see article of N. Foray et al., "A subset of ATM- and ATR-dependent phosphorylation events requires the BRCA1 protein", published in The EMBO Journal vol. 22(11), p. 2860-2871 (2003)). It has been attempted to use the ATM enzyme in an explanatory model of cell radiosensitivity (see Joubert et al., "DNA double-strand break repair defects in syndromes associated with acute radiation response; At least two different assays to predict intrinsic radiosensitivity?", published in Int. J. Radiat. Biol., vol. 84(2), p. 107-125 (2008)), and this made it possible to identify three types of radiosensitivity: radioresistant cells (Group I radiosensitivity), moderately radiosensitive cells (Group II radiosensitivity, and extremely radiosensitive cells (Group III radiosensitivity). However, no predictive model was proposed on this basis, in particular no relationship was established between the clinical data (tissue severity grade) and the radiobiological data. Similarly, the presentation of N. Foray, "Les réparatoses: nouveaux concepts sur la prédiction de la radiosensibilité", presented at "Rencontres Nucléaire & Santé" on Jan. 25, 2008 (XP55131242), suggests the role of the different markers pH2AX and MRE11 and the changes thereof over time for describing the number of radiation-induced double-strand breaks. This presentation does not mention the tissue severity grades, which quantify and identify the degree of radiosensitivity observed at the clinical level.

Numerous documents describe the conditions in which ATM may contribute to the detection and repair of DNA damage. The patent application WO 2004/013634 (KUDOS Pharmaceuticals Ltd.) describes the identification of an ATM-dependent DNA damage-signaling pathway that interacts with other DNA damage response factors, including the MRE11/Rad51/NBS1 complex. The patent application US 2007/0072210 (Ouchi and Aglipay) proposes a method for screening potential therapeutic agents that promotes a response to DNA damage, in which a protein called BAAT1 (that is associated with a predisposition to cancer associated with the BRCA1 gene), an ATM protein and the candidate compound are mixed; if the phosphorylation of ATM is increased with respect to a control mixture not containing the candidate compound, the latter is identified as being a potential active principle promoting DNA repair. The patent application EP 2 466 310 A1 (Helmholtz Zentrum München) describes the repair of DNA double-strand breaks in the presence of the phosphorylated form of H2AX histone (called gamma-H2AX or g-H2AX). The application WO 00/47760 and U.S. Pat. No. 7,279,290 (St. Jude's Children's Research Hospital) describe the role of the ATM kinase function in DNA repair.

These last documents therefore describe repair pathways but do not offer any correlation for establishing a clinical link.

Patent EP 1 616 011 B1 (International Centre for Genetic Engineering and Biotechnology) proposes a method for diagnosis of a genetic defect in DNA repair based on three steps: the culture of isolated cells of a sample to be tested, the incubation of said cells with a chimeric polypeptide, the characterization of the cell response. Said cell response is the expression level of a biochemical marker consisting of the following types of intracellular proteins: p53, ATM, Chk1, Chk2, BRCA1, BRCA2, Nbs1, MRE11, Rad50, Rad51 and histones. However, the radiation-induced expression cannot be predictive of the functionality of said proteins (certain syndromes have a normal expression level when the protein is mutated): these procedures are not functional tests.

The patent applications WO 01/90408, WO 2004/059004 and WO 2006/136686 (French Atomic Energy Commission) describe other methods for observing DNA damage resulting from ionizing radiation. The first document concerns the demonstration of DNA lesion incision activities, and does not enable the quantification of enzymatic activities of excision and re-synthesis of DNA or DSB repair. The two other documents describe the quantitative evaluation of the capacities of a biological medium to repair its DNA by means of circular supercoiled double-strand DNA (according to the third document: immobilized in a porous polyacrylamide hydrogel film). These methods do not directly concern DSBs in their in situ physiological environment and there is no correlation for validating their clinical application.

KR20030033519 proposes deducing sensitivity to radiation from the catalysis or superoxide dismutase activity, and KR20030033518 uses glutathione peroxidase or glucose 6-phosphate dehydrogenase. Such methods do not detect markers directly linked to DNA damage or repair.

Patent application US 2011/312514 (Dana Farber Cancer Institute) proposes using the detection of FANCD2 foci as a marker. Patent application US 2007/0264648 (National Institute of Radiological Sciences) proposes the use of DNA oligomers for predicting the appearance of adverse effects in radiotherapy. However, certain kinds of radiosensitivity may be observed when the FANCD2 foci level is normal.

Patent applications US 2008/234946 and US 2012/041908 (University of South Florida et al.) describe a method for predicting radiosensitivity of cancer cells and not healthy cells; it is also based on genomic data and not functional tests.

Patent application WO 2014/154854 (Centre Hospitalier Universitaire de Montpellier) describes a method for predicting radiosensitivity of a subject via the use of at least one radiosensitivity biomarker. This method does not detect markers directly linked to DNA damage or repair; it is also based on proteomic data. Moreover, this patent application does not describe a quantitative relationship between the radiobiological data and the severity of the tissue reactions.

Patent application WO 2013/187973 (University of California) describes systems and methods for determining the radiosensitivity of cells and/or of a subject with regard to a control population. More specifically, this method includes the irradiation of a biological sample, the detection and quantification of radiation-induced foci in erythrocytes, lymphocytes and primer cells, resulting from a blood sample via the use of one or more detection markers among a set of markers including anti-pH2AX, anti-MRE11 and anti-ATM. The quantification of radiation-induced foci at different post-irradiation observation times below 2 hours makes it possible to determine their repair kinetics, empirically correlated with the radiosensitivity of the subject. However, the analysis of foci in lymphocytes is very difficult due to their small nucleus. Moreover, this method does not enable the practitioner to make decisions regarding the treatment of the patient.

U.S. Pat. No. 8,269,163 (New York University School of Medicine) describes a large number of proteins capable of being used as markers for simply and rapidly assessing the significance of accidental exposure of a person to ionizing radiation, in order to triage patients and direct them to the appropriate emergency treatment. This last patent concerns biological dosimetry (determination of the accidental dose) while the detection of radiosensitivity is performed on the basis of a known dose.

Patent application WO 2010/88650 (University of Texas) describes methods and compositions for identifying cancer cells that are sensitive or resistant to a particular radiotherapy treatment; therefore, they are not applicable to just any radiotherapy treatment.

Patent application WO 2010/136942 (Philips) describes a general method for monitoring a patient during radiotherapy by means of biomarkers. The method includes obtaining at least one descriptor based on an image extracted from an imaging modality, in which the descriptor belongs to a tissue of interest for which radiotherapy is provided or to a tissue in the vicinity of the target volume. The method also includes the selection of at least one biological markers specific to a disease, capable of detecting or quantifying adverse effects of radiotherapy in the area of the tissues of interest. In addition, the method includes the recovery of at least one in vitro measurement value of the selected biomarker specific to the disease. In addition, the method includes the treatment of the at least one descriptor of the at least one in vitro biomarker value by means of a correlation technique, resulting in an output signal indicating radiotoxicity in the region of the tissue of interest. However, the teaching of this patent takes into account only the tissue-dependent toxicity and not the individual, and is primarily based on image analysis.

Patent application WO 2010/109357 describes a method and a device for planning an adaptive radiotherapy protocol based on the optimization of the probability of normal tissue complication and the probability of tumor control according to markers specific to each patient. The values of the markers associated with normal tissues include in vitro test values, signatures by mass spectrometry of proteins, and data of the patient's history. The in vitro test values may be of cellular, proteomic and genetic origin, such as, but without being limited to, various cell counts, HB, CRP, PSA, TNF-alpha, ferritin, transferrin, LDH, IL-6, hepcidin, creatinine, glucose, HbAlc, and telomere length. The patient's history markers include prior abdominal surgery, hormonal drugs or anticoagulants, diabetes, age and measurements associated with tumor growth. Biomarkers not associated with radiotoxicity are also envisaged, such as biomarkers associated with various forms of ablation or chemotherapy agents. However, individual radiosensitivity is not taken into account.

In spite of this vast prior art, the applicant notes that the above-described patents do not describe a method for quantification of individual radiosensitivity making it possible to evaluate the risk of post-radiotherapy tissue reactions, which may be used for any patient and any type of ionizing radiation capable of inducing DSB, and which is predictive. The problem of providing a method predicting individual radiosensitivity therefore has not operational solution. This invention is intended to propose a new method for predicting tissue and clinical radiosensitivity.

SUMMARY

The inventors have observed, and the method according to the invention is based on this observation, that double-strand breaks (DSB) of DNA constitute the radiation-induced damage with the greatest value of prediction of radiosensitivity when they are non-repaired and, and of prediction of genomic instability when they are poorly repaired. The inventors discovered that DSBs are managed by the major mode of repair, called joining, and/or by the minor mode of faulty repair called MRE11-dependent recombination. The balance between these modes of repair is controlled by the ATM protein. The pH2AX marker indicates a DSB site recognized by the joining repair mode. The MRE11 marker indicates a DSB site that has been managed by the faulty MRE11-dependent repair. The pATM marker provides information on the activation of the joining pathway by H2AX phosphorylation and inhibition of the MRE11-dependent pathway.

The inventors have also observed a transfer of the cytoplasmic forms of the ATM protein in the cell nucleus after oxidative stress, and in particular after stress related to ionizing radiation inducing DSBs.

To observe DNA damage by exogenous stress, it is necessary to take into account, on the one hand, the spontaneous state of the DNA, and, on the other hand, the radiation-induced state thereof. Moreover, after irradiation, it is necessary to take into account DNA repair, the kinetics of which are dependent upon the repair mechanism and therefore the type of radiation-induced damage. It is also known that the efficacy and speed of the DNA repair varies from one individual to another, and that there are also particular genetic conditions that lead to exceptional radiosensitivity.

According to the invention, the problem is solved by a method based on: 1) amplification of non-transformed cells, in particular cells from skin biopsies; 2) a mechanistic model valid for quiescent human cells; 3) functional tests for recognition, repair and signaling of the DSBs valid regardless of the therapeutic modality.

A first object of the invention is a method for predicting cellular radiosensitivity of a cell sample to ionizing radiation, said cell sample having been obtained from cells sampled from a patient in a non-irradiated or slightly-irradiated area, in which method:

(i) said sampled cells are amplified, said amplified cells forming "the cell sample";

(ii) on said cell sample, the mean number of nuclear foci obtained is determined with the pH2AX marker at the observation time t (this mean number being called NpH2AX(t)), said observation time t being the time t=0 min (called t0, non-irradiated state) and the observation time t4 (and preferably also times t1, t2 and t3) after irradiation with an absorbed dose D;

(iii) the total dose not to be exceeded (TDNTBE) is determined, expressed in Gray (Gy), using at least the parameter NpH2AX(t4), (iv) on said cell sample, the mean number of nuclear foci obtained is determined with at least two markers pH2AX, pATM and MRE11 at observation time t (said mean numbers being called, respectively, NpH2AX(t)), NpATM(t)), NMRE11(t)), said observation times t being the time t=0 min (called t0, non-irradiated state) and at least one observation time selected from t=t1, t2, t3 and t4 after irradiation with an absorbed dose D;

(v) the radiosensitivity group of the sample is determined using at least the mean numbers NpH2AX(t)), NpATM(t)) and NMRE11(t));

and in which method:

t4 is a fixed value that represents the time for which the DNA break level reaches its residual value, and which is advantageously chosen between 6 times t3 and 8 times t3, but must be in this case at least 12 hours, and preferably between 12 h and 48 h, and which is more preferably around 24 hours;

t3 is a fixed value that represents the time after which around 25% of the DSBs are repaired in control cells from radioresistant patients, and which is advantageously chosen between 3 times t2 and 5 times t2, but must in this case be at least 2.5 hours and at most 6 hours, and is preferably between 3 hours and 5 hours, and is more preferably around 4 hours;

t2 is a fixed value that represents the time after which around 50% of the DSBs are repaired in control cells from radioresistant patients, and which is advantageously chosen between 5 times t1 and 7 times t1, but which must in this case be at least 35 minutes and at most 90 minutes, and is preferably between 45 minutes and 75 minutes, and is more preferably around 60 minutes;

t1 is a fixed value that represents the time after which the number of recognized DSBs reaches its maximum in control cells from radioresistant patients, and which is advantageously chosen between 5 minutes and 15 minutes after the irradiation has been stopped, preferably between 7.5 minutes and 12.5 minutes, and even more preferably at around 10 minutes.

In an advantageous embodiment, the mean number of nuclear foci obtained with the pH2AX marker at observation times t1, t2 and t3 is also used in order to verify the form of the DSB kinetic recognition and repair curve.

The total dose not to be exceeded (TDNTBE), expressed in Gray (Gy), is an important parameter for the radiotherapist, which makes it possible to predict which maximum dose a given patient may absorb without a potentially lethal reaction; this parameter also makes it possible to void radiotherapy in patients with particularly high radiosensitivity.

TDNTBE is ideally expressed as a skin equivalent: as experiments are performed on cutaneous fibroblasts, it cannot be directly quantitatively extrapolated to other tissues. Predictions therefore concern essentially the radiation-induced response of skin or a biological equivalent tissue (example: lung fibroblasts). However, extrapolations to other tissues such as the endothelium, astrocytes or epitheliums may be performed qualitatively while we await a more precise definition of corrective factors specific to each tissue.

According to the invention, it is possible to determine TDNTBE according to the formula:

$$TDNTBE=60/NpH2AX(t4) \text{ if } NpH2AX(t0) \leq 3,$$

or according to the formula:

$$TDNTBE=60/[NpH2AX(t4)+NpH2AX(t0)] \text{ if } NpH2AX(t0)>3.$$

In a variant of the method according to the invention, it is also determined, on said cell sample, the mean number of micronuclei observed at time t for 100 cells [in %] (said mean number being called NMN(t)), the time t being at least t0 (non-irradiated) and t4 after irradiation with an absorbed dose D, the parameter NMN(t4) is used to determine the TDNTBE. However, as the statistical uncertainty of the experimental micronuclei measurement is greater than that of the number of nuclear foci observed by immunofluorescence, the predictive values of the measurement of foci will be preferred to that of the micronuclei.

Thus, for example, it is possible to determine the TDNTBE on the basis of NMN(t) according to the formula:

TDNTBE=60/[0.4×NMN(t4)], if NpH2AX(t0)≤3, or according to the formula:

TDNTBE=60/[2+(0.4×NMN(t4))], if NpH2AX(t0)>3.

The use of one or the other variants of the method according to the invention leads to a decimal number. The value of the final TDNTBE, obtained after use of one or the other of the formulas is a whole number corresponding to the arithmetic rounding of the value obtained by calculation. The TDNTBE determined according to the invention corresponds to this whole number.

In a variant of the method according to the invention, advantageously, the radiosensitivity group of the patient is determined before that of the TDNTBE in order to assign a correct TDNTBE value to the patient for patients belonging to type-II radiosensitivity group (moderate radiosensitivity).

The radiosensitivity group of the sample was determined via the formulas described above, as follows:

(a) the sample is considered to be radioresistant if NpH2AX(t4)<2 and NpATM(t1)>NpATM(t2) and NpATM(t1)>30 and A<10 and B<5 and C<2; with:
C=NpH2AX(t0)+NMN(t0);
B=% large nuclei (greater than 150 μm2) at t0;
A=NMRE11(t0)+Number of small pH2AX foci per cell at t0;

(b) the sample is considered to be highly radiosensitive if (NpH2AX(t4)>8 or NMN(t4)>24);

(c) the sample is considered to have moderate radiosensitivity for all other conditions.

For certain patients, the DNA repair may be disrupted by an incessant production of spontaneous DNA double-strand breaks (DSB) due to the phenomenon of hyper-recombination, which is generally observed in patients predisposed to cancer. The spontaneous overproduction of DSB may have two effects that are non-contradictory: in the spontaneous state and by pH2AX marking, nuclear foci smaller than the pH2AX foci normally observed may appear; they are a reflection of the presence of a large number of DSB ("small foci" phenomenon). Similarly, an overproduction of DSBs may lead to decondensation of chromatin, which increases the size of the cell nucleus (size generally greater than 150 μm2, corresponding to the "large nuclei" phenomenon). These two phenomena are a reflection of high genomic instability.

The TDNTBE is then determined for patients of radiosensitivity group II via the two variants presented above, namely according to formula:

TDNTBE=60/NpH2AX(t4), if NpH2AX(t0)≤3, or according to the formula:

TDNTBE=60/[[NpH2AX(t4)]+NpH2AX(t0)] if NpH2AX(t0)>3, or according to a second variant, it is possible to determine the TDNTBE on the basis of NMN(t) according to the formula:

TDNTBE=60/[0.4×NMN(t4)], if NpH2AX(t0)≤3, or according to the formula:

TDNTBE=60/[2+(0.4×NMN(t4))], if NpH2AX(t0)>3.

The use of one or the other variant of the method according to the invention leads to a decimal number. The value of the final TDNTBE, obtained after use of one or the other of the formulas is a whole number corresponding to the arithmetic rounding of the value obtained by calculation. The TDNTBE determined according to the invention corresponds to this whole number.

The method according to the invention uses at least one healthy tissue sample, preferably fibroblasts. The latter are preferably sampled from the connective tissue of the patient. This sampling may be performed by biopsy. Thus, in an advantageous embodiment, said sampled cells are fibroblast cells from a skin biopsy of a patient (typically sampled according to a method known as a "skin punch biopsy"). The tissue sample is cultivated in an appropriate culture medium.

The first step of the method according to the invention following the sampling of the cells (namely in the embodiment preferred via the establishment of the biopsy of the fibroblast line) consist in characterizing the spontaneous DNA state (state at t0), i.e. without irradiation. This step may comprise in particular the examination of the nucleus size, the presence of micronuclei, any spontaneous apoptotic bodies and multilysed cells: the cells are observed under a fluorescence microscope. Using DAPI stain (4'6'-diamidino-2-phenylindole, CAS no. 28718-90-3 for dihydrochloride), the micronuclei level for 100 cells, which is an indicator of genomic instability, is determined. The apoptotic bodies are also determined. The population of abnormally large nuclei, the presence of which indicates chromatin decondensation, is also determined.

Said ionizing radiation is defined by the absorbed dose (parameter called D and expressed in Gray). In the context of the present invention, the absorbed dose D is between 0.5 Gy and 4 Gy, preferably between 1 Gy and 3 Gy, preferably between 1.7 Gy and 2.3 Gy, and is even more preferably 2 Gy. These ranges typically correspond to an individual radiotherapy treatment session, the number of sessions depending upon the location, type and stage of advancement of the tumor.

It is essential in the method according to the invention that all of the time values t1, t2, t3 and t4 be defined at the start of a series of tests (i.e. at least for a given patient, and preferably for a plurality of patients in order to calibrate the method with respect to a set of statistically significant observations) and that they be the same for all determinations of all parameters referring to said time intervals.

In the method according to the invention, t1 is advantageously between 8 minutes and 12 minutes and/or t2 is advantageously between 50 minutes and 70 minutes, and/or t3 is advantageously between 3.5 hours and 4.5 hours, and/or t4 is advantageously between 22 hours and 26 hours; preferably all four of these conditions are satisfied.

In a particularly beneficial and easily standardized variant of the method, t1 is 10 minutes, t2 is 60 minutes, t3 is 4 hours, t4 is 24 hours, and D is 2 Gy.

The determination of NpH2AX(t) advantageously involves an immunofluorescence test.

The control cells from radioresistant patients may be sampled from patients selected on the basis of a clinical examination, such as patients not having shown significant tissue reactions during or after a radiotherapy treatment. They may also be selected as cells showing an in vitro clonogenic survival rate greater than 55% after irradiation with an absorbed dose of 2 Gy.

We will now describe a typical embodiment.

Cells are observed with the pH2AX marker. It is possible to add observations with pATM and/or MRE11 markers at observation times t (these mean numbers being called, respectively, NpATM(t) and NMRE11(t)) and at least one observation time selected from t=t1, t2, t3 and t4 after irradiation with an adsorbed dose D. In one embodiment, the number of foci is determined with the pH2AX marker and the presence of multilysed cells. The locations of the pATM protein and of the MRE11 protein (nuclear or cytoplasmic) are noted.

This first step makes it possible to identify possible genomic instability in the spontaneous state.

The second step of the method according to the invention includes irradiation with the desired absorbed dose D (for example 2 Gy) and the evaluation of the cell response to ionizing radiation.

a) In a first embodiment, the repair of radiation-induced DSBs by joining, which is the major mode of repair, is studied. The number of pH2AX foci per cell at t4 and optionally also at t1, t2, and possibly also at t3 is determined; the determination at t3 makes it possible to consolidate the definition of the rate of the kinetics from t1 to t4. In an advantageous embodiment, after the time t4, the micronuclei level is also determined in order to deduce the level of radiation-induced micronuclei. This makes it possible to estimate the radiosensitivity according to the significance of the non-repaired DSBs.

b) In a second embodiment, the cell response to ionizing radiation through the measurement of the functionality of the ATM-dependent kinase activity is studied in greater depth. It is known that in control radioresistant cells, the phosphorylated forms of the ATM protein (pATM) are cytoplasmic in the spontaneous state. The applicant discovered that, in the irradiated state, they have a tendency to become nuclear. Once they have passed into the nucleus, the pATM forms activate the joining repair mechanisms and inhibit the faulty MRE11-dependent repair pathway.

As an example, if, after irradiation (for example with an absorbed dose of 2 Gy), the pATM forms show a cytoplasmic localization, it is concluded that the pATM forms do not pass or cannot pass normally from the cytoplasm to the nucleus. This may be caused by a mutation of ATM or any other ATM protein partner that would help it to pass into the nucleus after irradiation: in any case, this indicates significant radiosensitivity.

This optional determination of the location of the pATM protein is performed at least at t1 and t2, and optionally also at t3 and t4.

c) In a third embodiment capable of being combined with the previous ones, the cell response to ionizing radiation through the MRE11-dependent pathway is studied further. In addition to the major joining repair pathway, the capacity of which can be quantified by pH2AX immunofluorescence, the applicant identified another repair pathway, alternative to the joining pathway, and which is capable of replacing it in the case of a deficiency: it is repair by MRE11-dependent recombination. Its capacity can be quantified by the kinetic study of the immunofluorescence of MRE11 foci. This measurement is performed at least at t1, t2 and t3, and optionally also at t4. According to the applicant's observations, in the radioresistant control lines, MRE11 is cytoplasmic and the number of MRE11 foci is very low until 4 hours after a 2-Gy dose (typically 7±2 MRE11 foci); the marking becomes cytoplasmic around 24 hours after irradiation.

In a final step, the results are evaluated by calculating the scores in order to predict the state of radiation-induced damage and/or the radiosensitivity of the patient, and in particular the TDNTBE specific to the patient.

DRAWINGS

FIGS. 1(A), 1(B), and 1(C) respectively illustrate the change in the number of foci of the micronuclei (a), of markers pH2AX (b) and pATM (c) from non-irradiated cells as a function of the severity grade according to the CTCAE classification.

FIGS. 2(A) and 2(B) respectively illustrate the change in the number of micronuclei 24 hours after irradiation according to the CTCAE (FIG. 2(A)) or RTOG (FIG. 2(B)) severity grades.

FIGS. 3(A), 3(B), and 3(C) respectively illustrate the kinetics of the mean number of foci obtained with the pH2AX marker over time, and the change in the number of pH2AX foci 24 hours after irradiation as a function of the CTCAE (FIG. 3(B)) or RTOG (FIG. 3(C)) severity grades.

Figure 5A:
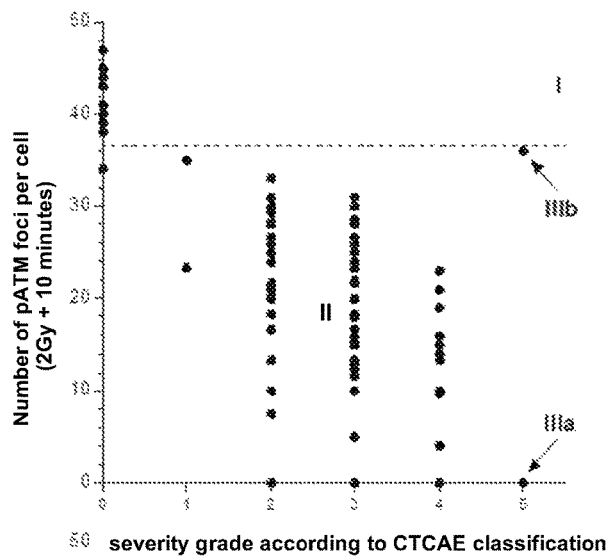
Figure 5B:
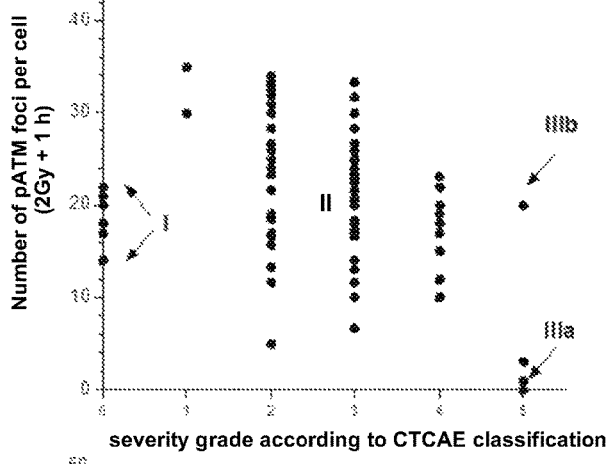
Figure 5C:
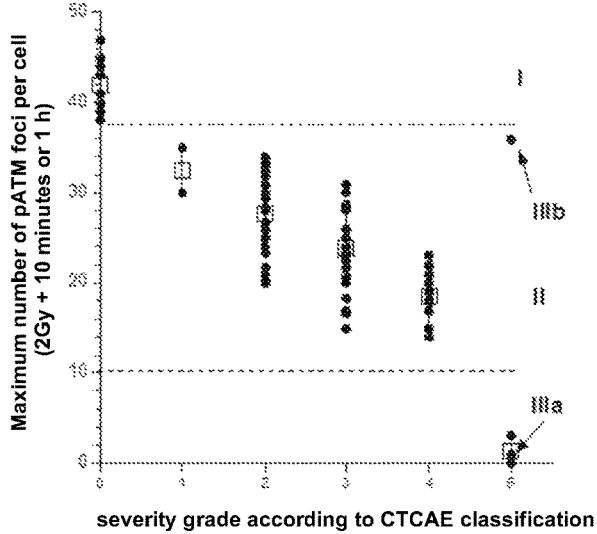

FIGS. 5(A), 5(B), and 5(C) respectively illustrate the change in the number of pATM foci as a function of CTCAE severity grades after 10 minutes (FIG. 5(A)) and 1 hour following an irradiation with 2 Gy (FIG. 5(B)), and the maximum number of pATM foci between the 2 values obtained at 10 minutes and 24 hours after a 2-Gy irradiation as a function of the CTCAE severity grades.

Figure 6A:
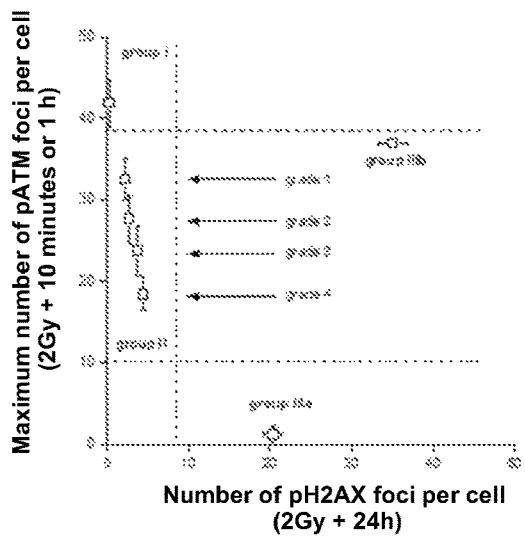

FIG. 6(A) illustrates the maximum number of foci obtained with the pATM marker as a function of the number of pH2AX foci.

Figure 6B:
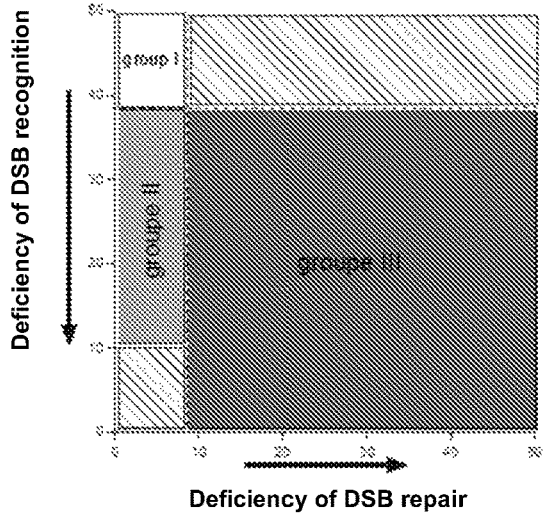

FIG. 6(B) illustrates the well-defined confidence intervals representing the different groups of human radiosensitivity (Group I, Group II and Group III).

Figure 6C:
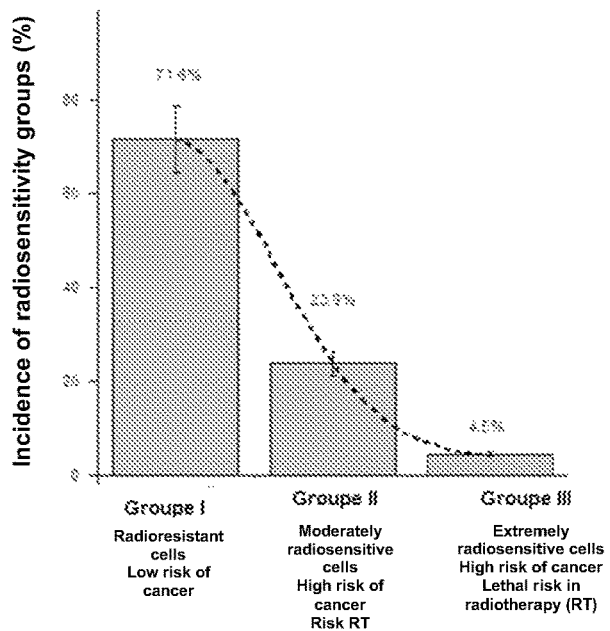

FIG. 6(C) illustrates the incidence of the groups for each type of group.

Figure 1A:
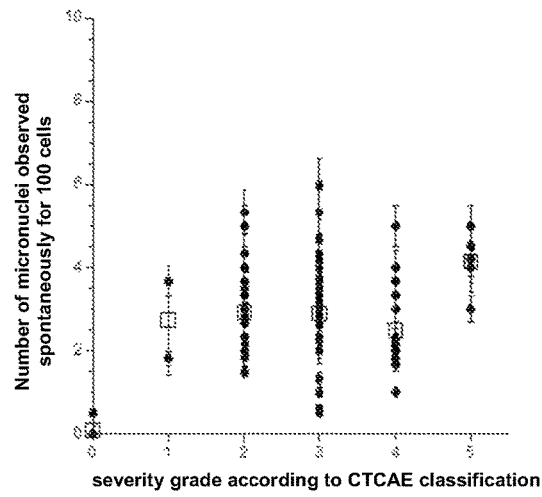
Figure 1B:
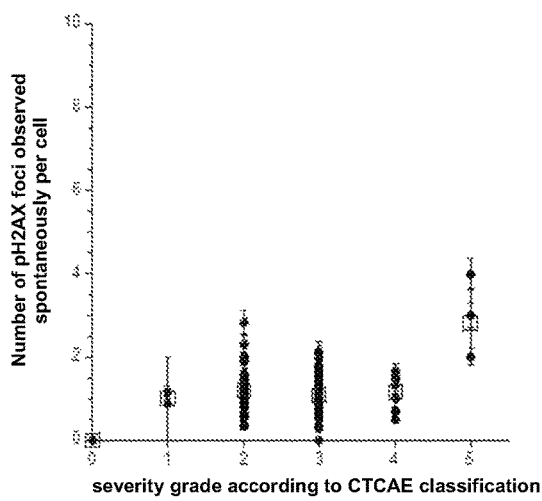
Figure 1C:
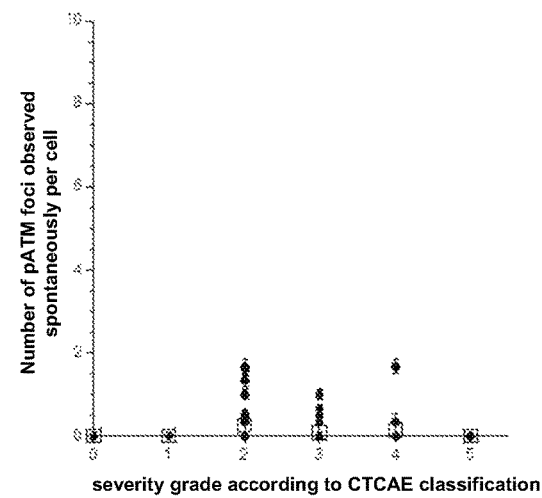

FIGS. 1(*a*), (*b*) and (*c*) respectively show the change in the number of foci of the micronuclei (a), of markers pH2AX (b) and pATM (c) from non-irradiated cells as a function of the severity grade according to the CTCAE classification. The micronuclei, the pH2AX and pATM foci from non-irradiated cells are not predictive of radiosensitivity.

Two different scales of severity of tissue reactions coexist: the CTCAE classification and the RTOG classification.

The so-called CTCAE classification (Common Terminology Criteria for Adverse Events), published in 2006 by the National Cancer Institute of the United States of America, is a descriptive terminology of adverse events (in particular adverse effects) in cancer therapy.

An adverse event corresponds to any unfavorable and involuntary sign, symptom or disease associated in time with the use of a medical treatment or procedure that may or may not be considered to be associated with the medical treatment or procedure. An adverse event is a unique representation of a specific event used for medical documentation and in scientific analyses.

The CTCAE provides a brief definition of each adverse event in order to clarify the meaning of the adverse event. This scale, valid for other genotoxic stresses (for example: burn wounds) is particularly used in radiotherapy.

The grade refers to the severity of the adverse event. The CTCAE has 5 severity grades (from 1 to 5) with unique clinical severity descriptions for each adverse event, described in table 1 below. Each severity grade is defined by specific tissue reactions.

TABLE 1 most recent version of the CTCAE scale published by the National Cancer Institute of the United States of America on Jun. 14, 2010.

Grade 1 Mild severity; asymptomatic or mild symptoms; clinical or diagnostic observations only; intervention not indicated
Grade 2 Moderate severity; minimum, local or non-invasive action indicated; limiting age-appropriate instrumental activities of daily living (preparing meals, shopping, using the telephone, etc.)
Grade 3 Serious or medically significant severity, but not immediately life-threatening; hospitalization or prolongation of hospitalization indicated; disabling event; event limiting self care activities of daily living (bathing, dressing, feeding self, using the toilet, taking medication, and not bedridden)
Grade 4 Life-threatening consequences; urgent intervention indicated
Grade 5 Death related to the adverse event To these 5 grades, a grade 0 corresponding to an absence of tissue effect is added.

The historic so-called RTOG classification, proposed by the Radiation Therapy Oncology Group (RTOG) in 1984 covers practically all types of toxicities developing after radiotherapy.

However, the RTOG classification is not applicable to certain types of cancer, while the CTCAE is used for any type of cancer.

DESCRIPTION

Figure 2A:
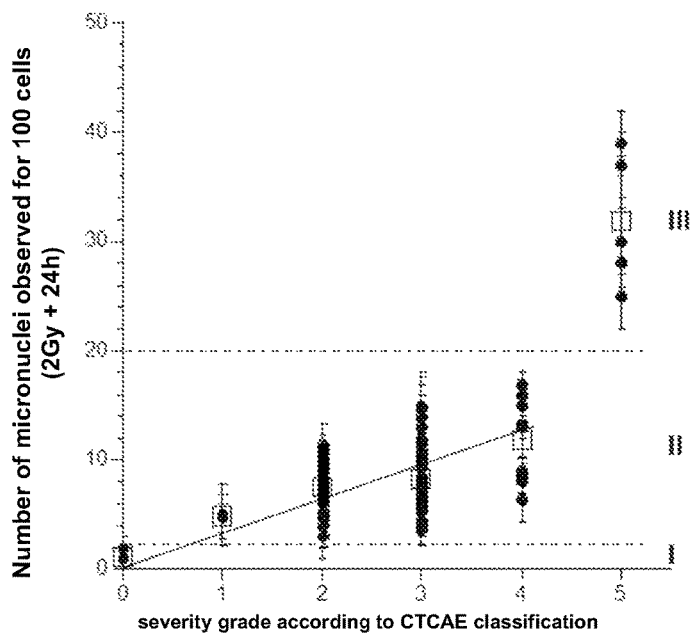
Figure 2B:
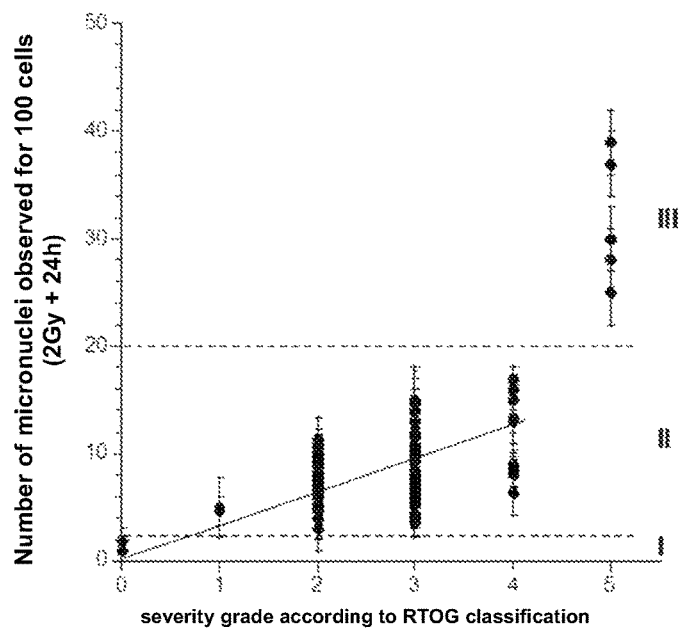

FIGS. 2(a) and 2(b) show the change in the number of micronuclei 24 hours after irradiation according to the CTCAE (FIG. 2(a)) or RTOG (FIG. 2(b)) severity grades. The micronuclei are marked with the DAPI fluorescent marker, then quantified by analysis of the fluorescence signal. The radiosensitivity group (I, II, III) is indicated in Roman characters in FIG. 2.

The number of micronuclei observed 24 hours after irradiation makes it possible only to predict the radiosensitivities of group III.

Figure 3A:
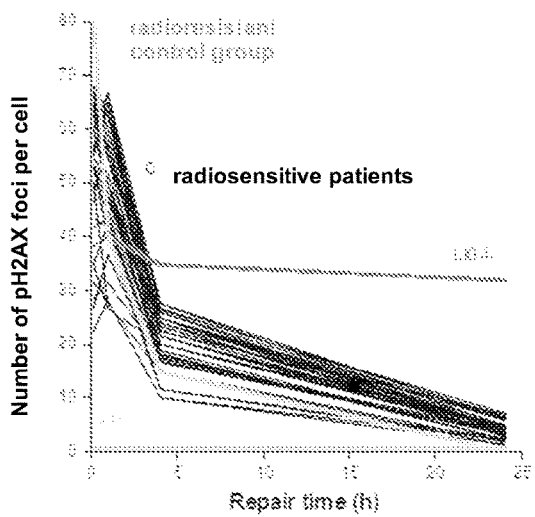
Figure 3B:
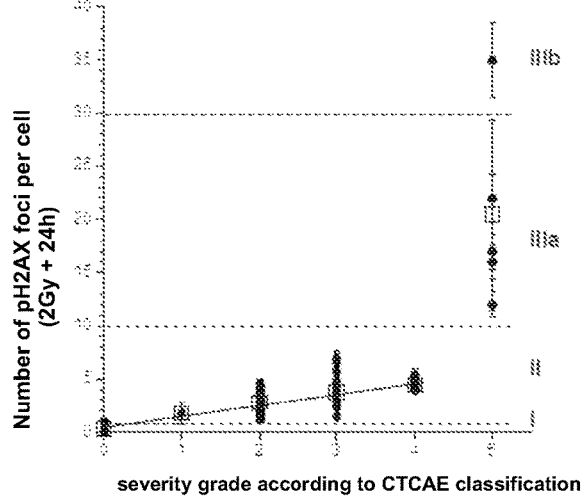
Figure 3C:
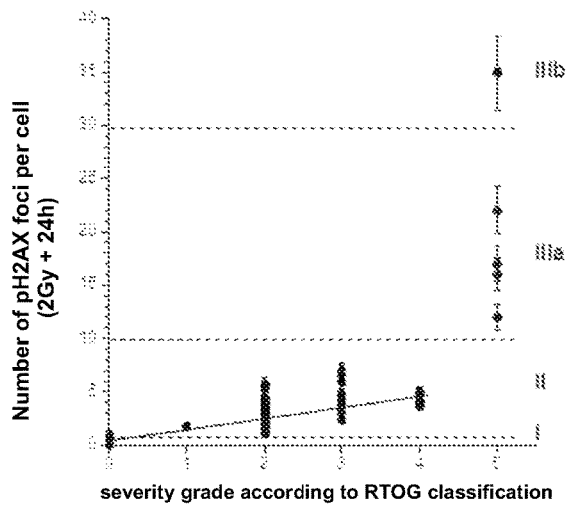

FIGS. 3(a), (b) and (c) show the change in the number of pH2AX foci 24 hours after irradiation as a function of the CTCAE (FIG. 3(b)) or RTOG (FIG. 3(c)) severity grades. FIG. 3(a) shows the kinetics of the mean number of foci obtained with the pH2AX marker over time.

The number of pH2AX foci obtained 24 hours after irradiation as a function of the CTCAE or RTOG severity grades (2 different scales of severity of tissue reactions) make it possible to predict only the radiosensitivities of group I, II or III, but not the severity grades.

Figure 4A:
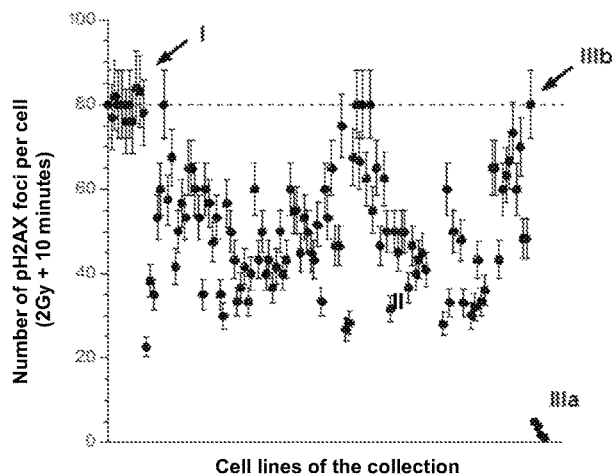
FIG. 4(A) illustrates the mean number of foci obtained with the pH2AX marker 10 minutes after irradiation with 2 Gy for all of the cell lines of a collection of patient samples (skin fibroblasts).

FIG. 4(A) shows the mean number of foci obtained with the pH2AX marker 10 minutes after irradiation with 2 Gy for all of the cell lines of a collection of patient samples (skin fibroblasts), the dotted line indicating the normal incidence of DSB, which is 40 DSB per Gy per cell.

FIG. 4(A) shows that all of the cells from patients with radiosensitivity of group II are characterized by fewer pH2AX foci (DNA double-strand breaks (DSB)) than expected after 2 Gy. This is explained by the fact that DSBs are insufficiently recognized.

Figure 4B:
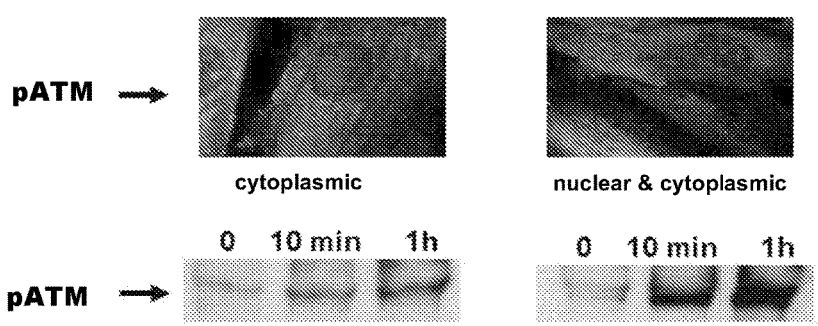
FIG. 4(B) illustrates the expression of pATMs in the cytoplasm and the nucleus at different times (0 minute, 10 minutes and 1 hour) after an irradiation with 2 Gy.

FIG. 4(B) shows the expression of pATMs in the cytoplasm and the nucleus at different times (0 minute, 10 minutes and 1 hour) after an irradiation with 2 Gy. The corresponding immunofluorescence data are presented for non-irradiated cells and for cells irradiated with 2 Gy at 10 minutes post-irradiation.

The data presented in FIG. 4(B), relating to the number of pATM foci, suggest a "cyto-nuclear transit" of the ATM.

Figure 4C:
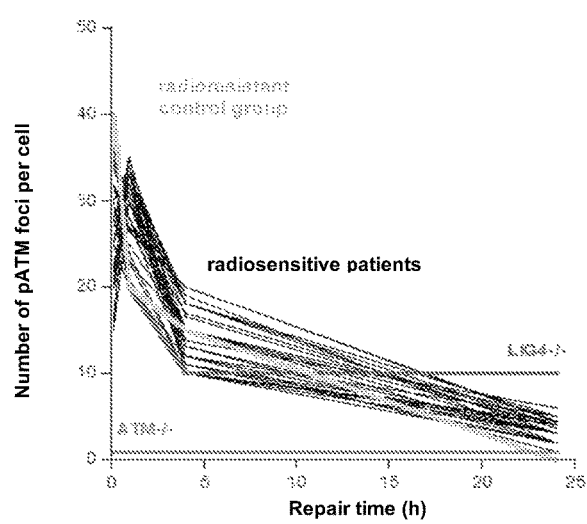
FIG. 4(C) shows the kinetics of the mean number of foci obtained with the pATM marker over time based on cells in the collection.

FIG. 4(C) shows the kinetics of the mean number of foci obtained with the pATM marker over time based on cells in the collection. For convenience, the error bars relating to the measurements performed at 10 min, 1 hour, 4 hours and 24 hours have been omitted. For FIGS. 4(A) and 4(C), each point represents the mean of three independent repetitions and the error bars represent the standard deviation for each category.

FIG. 5 shows the change in the number of pATM foci as a function of CTCAE severity grades after 10 minutes (FIG. 5(A)) and 1 hour following an irradiation with 2 Gy (FIG. 5(B)). FIG. 5(C) shows the maximum number of pATM foci between the 2 values obtained at 10 minutes and 24 hours after a 2-Gy irradiation as a function of the CTCAE severity grades, and presented previously in FIGS. 5(A) and 5(B), respectively.

FIG. 5(B) shows a grade 0, i.e. an absence of tissue effect.

FIG. 5(C) shows, for one hundred patients, the link between these radiobiological parameters and the severity grades according to the CTCAE classification. FIG. 5(C) thus shows the clinical validation of the correlation between the CTCAE severity grades and the maximum number of pATM foci between the 2 values obtained 10 minutes and 1 hour after an irradiation with 2 Gy.

The radiosensitivity groups (I, II, IIIa and IIIb) are indicated in Roman characters in FIG. 5. For FIGS. 5(A), 5(B) and 5(C), each point represents the mean of three independent repetitions for each category.

The maximum number of pATM foci between (2 Gy+10 min) or (2 Gy+1 h) makes it possible to predict all of the groups as well as the severity grade of the reaction.

FIG. 6(A) shows the maximum number of foci obtained with the pATM marker as a function of the number of pH2AX foci, previously shown in FIGS. 3(B) and 5(C), respectively.

FIG. 6(B) shows the data presented in FIG. 6(A) and shows the well-defined confidence intervals representing the different groups of human radiosensitivity (Group I, Group II and Group III). The radiosensitivity is determined by the recognition and repair of double-strand breaks.

FIG. 6(C) shows the incidence of the groups for each type of group. Considering that the probability of belonging to a given group is proportional to the inverse of the corresponding confidence intervals, the standardized frequency of each group is represented in FIG. 6(C) by bars. The dotted line corresponds to the Gaussian producing the best data adjustment ($r=0.9$).

A. General Definitions

The terms "radiation-induced damage", "radiation-induced", "radiosensitivity", "radioresistance", "radiotoxicity", "radiotherapy" all refer to ionizing radiation, in particular particle radiation, as constituted by alpha (α) or beta (β) particles, or high-energy electromagnetic radiation, in particular gamma ( ) or X-rays.

The term ATM cyto-nuclear transit describes the translocation performed by the ATM protein passing from the cytoplasm to the nucleus, in particular after irradiation.

DETAILED DESCRIPTION

We will now describe an embodiment with multiple variants appropriate to a human patient.

1. Preparation of the Test

Before any sampling of cells and before any handling of the cells sampled, the respective operators (belonging, for example, to a cytological analysis laboratory) are informed (typically by the physician) of the possible HIV or hepatitis C infection status of the patient so that the operators may take the appropriate biological safety measures during sampling, handling and management of the cell culture.

Then, the operator takes a cell sample from the patient. Preferably, the operator takes it by biopsy of a skin sample; this sampling may advantageously be performed according to a method known as "skin punch biopsy". The cell sample is placed in the sterile fetal bovine serum DMEM+20% medium. The sample is then immediately transferred to a specialized laboratory, with the understanding that the sample must not remain for longer than 38 hours at room temperature.

Upon receipt, the cell sample (typically biopsy) is established in the form of an amplifiable cell line without a viral or chemical transformation agent according to an ancillary and well known procedure of culture laboratories, as emphasized by the publication of Elkin M. et al. "The radiobiology of cultured mammalian cells", Gordon and Breach (1967). Once the number of cells is sufficient (1 week-3 weeks), the first experiments are performed using the method according to the invention. The cells are seeded on glass slides in Petri dishes. Some of these slides are irradiated on a medical irradiator according to a certified dosimetry with an absorbed dose D (for example, 2 Gy). Others are not irradiated; these represent the spontaneous state (absorbed dose 0 Gy).

The irradiation may be performed, for example, with a medical accelerator that delivers 6 MV photons with an absorbed dose rate of 3 Gy min-1. After irradiation and to survive the repair times mentioned below, the cells remain in a culture incubator at 37° C.

For the irradiated cells, characteristics corresponding to the radiation-induced state are acquired after multiple repair times (post-irradiation repair times). Preferably, at least two and even more preferably at least three points are acquired, namely: t1, t2, t3 and t4. Said characteristics are represented by the foci corresponding to the pH2AX marker.

The cells on glass slides are then fixed, lysed and hybridized. The following procedure, known as such (see the cited publication of Bodgi et al.), may be used: the cells were fixed in 3% paraformaldehyde and 2% sucrose for 15 minutes at room temperature and permeabilized in 20 mM of HEPES buffer solution (4-(2-hydroxyethyl)-1-piperazine ethane sulfonic acid) at pH 7.4, 50 mM NaCl, 3 mM MgCl2, 300 mM sucrose, 0.5% Triton X-100 (a nonionic surfactant of formula t-Oct-C6H4-(OCH2CH2)xOH with x=9-10, CAS No. 9002-93-1, supplied by Sigma Aldrich) for 3 minutes. Then, the cover slides were washed in phosphate-buffered saline (known as PBS) before immunological staining. The incubation took place for 40 minutes at 37° C. in PBS to which 2% bovine serum albumin (known as BSA or fraction V, supplied by Sigma Aldrich) was added, followed by a PBS washing. The primary anti-pH2AX antibodies were used at a concentration of 1:800, the other primary antibodies at 1:100. The incubations with secondary anti-mouse FITC or anti-rabbit TRITC antibodies (1:100, supplied by Sigma Aldrich) were performed at 37° C. in BSA at 2% for 20 minutes. Glass slides were treated with Vectashield™ containing DAPI (4,6-Diamidino-2-phenylindole) to mark the nucleus. The staining with DAPI also enables, indirectly, the determination of the number of cells in the G1 phase (nuclei with homogeneous DAPI staining), in the S phase (nuclei with numerous pH2AX foci), in the G2 phase (nuclei with heterogeneous DAPI staining) and metaphases (visible chromosomes).

The results are acquired from these slides on immunofluorescence microscope (Olympus model, for example). The reading may be direct (typically by counting foci on at least 50 cells in G0/G1 for each point) or by dedicated image analysis software, or on an automated microscope; preferably the software or automated microscope methods are calibrated with manual determinations.

To obtain results of statistical reliability sufficient to serve as a basis for a diagnosis, at least 3 independent series of experiments (irradiation) are performed and the mean of each of the numbers of foci for the times defined is calculated.

2. Determination of Biological and Clinical Parameters 2.1 Generalities and Markers Used The invention is based, inter alia, on the use of data acquired for the pH2AX marker on non-irradiated cells (spontaneous state) and irradiated cells (radiation-induced state). The method is based on the kinetic study of the marking by said marker as a function of the repair time: the samples are marked after a predetermined time lapse starting from the stop of irradiation, and their immunofluorescence is studied. It is possible to measure complete kinetic curves, for example represented by 5 points located advantageously at t0, t1 (preferably 10 minutes), t2 (preferably 1 hour), t3 (preferably 4 hours) and t4 (preferably 24 hours), with the understanding that t0 corresponds to the state before irradiation (spontaneous state). It is advantageous to associate the data acquired with two other markers, namely pATM and MRE11.

However, the applicant realized that certain points (corresponding to certain repair times) are more important than others, and that certain points are not predictive. Owing to the careful selection of parameters determined at given times, it is thus possible to reduce the number of measurements and therefore reduce the overall cost of the diagnosis, without diminishing the predictive power of the method. It is this simplified method that constitutes the basis of the predictive method according to the invention.

The means of each point and each dose with each marker are calculated with standard errors of the mean (SEM), with the sampling being n=3 (not a Gaussian standard error SE).

(i) pH2AX designates the phosphorylated forms in Serine 439 of variant X of the H2AX histone that marks, according to the applicant's observations, the number of DNA double-strand breaks (DSB) recognized by the major and reliable repair mode, joining. The pH2AX marker is essentially nuclear, in the form only of nuclear foci and only the number and size of the foci will be analyzed.

(ii) pATM designates the phosphorylated forms in Serine 1981 of the ATM kinase protein. According to the applicant's observations, ATM passes from the cytoplasm to the nucleus after irradiation under normal conditions (radioresistant status). The pATM forms are concentrated primarily in the cytoplasm, then mark DSB sites. The pATM marker is distinguished by a localization that may be homogenous cytoplasmic (no cytoplasmic foci) without nuclear foci, only nuclear in the form only of nuclear foci (no homogeneous nuclear localization), or cytoplasmic and nuclear foci.

(iii) MRE11 is an endonuclease that breaks DNA. According to the applicant's observations, MRE11 marks poorly repaired DSBs when the repair process is finalized. The MRE11 marker may be cytoplasmic without foci or cytoplasmic and nuclear without foci, or cytoplasmic and nuclear with foci.

The counterstaining with DAPI (a DNA marker known to a person skilled in the art) makes it possible to locate the nucleus in order to locate the cytoplasmic or nuclear localization (this distribution being modified for MRE11 and pATM under the influence of ionizing radiation), to quantify the micronuclei, the apoptotic bodies and the size of the nuclei which are complementary cell markers to the data on the foci.

2.2 Biological Parameters

The following are defined and determined as indicated:
NpH2AX(t), NpATM(t), NMRE11(t) the mean numbers of nuclear foci obtained with the markers pH2AX, pATM, and MRE11 at observation times t0 (non-irradiated) or t1, t2, t3, t4 after irradiation (absorbed dose: 2 Gy), with the understanding that the determination of the parameter NpH2AX(t) is obligatory in the context of the method according to the invention, while that of the other parameters NpATM(t) and NMRE11(t) is optional but advantageous;

the number of micronuclei observed spontaneously (at t=t0, i.e. without irradiation) or at t=t4 after irradiation with an absorbed dose of 2 Gy for 100 cells (in %).

2.3 Predictive Evaluation

The aim is to predict clinical or radiotherapy parameters on the basis of biological data measured. It involves a quantitative analysis directly based on the mathematical value of the scores or mathematical formulas linking the scores; the analysis concerns the total dose not to be exceeded in order to avoid a potentially lethal reaction (criterion referred to as TDNTBE) applicable to a patient who will undergo or who is undergoing radiotherapy.

The total dose not to be exceeded (TDNTBE), expressed in Gray (Gy), is an important parameter for the radiotherapist, which makes it possible to predict the maximum dose that a given patient may absorb without having a potentially lethal reaction; this parameter also makes it possible to avoid radiotherapy in patients with particularly high radiosensitivity.

According to the invention, it possible to determine the TDNTBE according to the formula:

$$TDNTBE=60/NpH2AX(t4) \text{ if } NpH2AX(t0) \leq 3,$$

or according to the formula:

$$TDNTBE=60/[NpH2AX(t4)+NpH2AX(t0)] \text{ if } NpH2AX(t0) > 3.$$

In a variant of the method according to the invention, it is determined, on said cell sample, the mean number of micronuclei observed at time t for 100 cells [in %] (said mean number being called NMN(t)), the time t being at least t0 (non-irradiated) and t4 after irradiation with an absorbed dose D, the parameter NMN(t4) is used to determine the TDNTBE. However, as the statistical uncertainty of the experimental micronuclei measurement is greater than that of the number of nuclear foci observed by immunofluorescence, the predictive values of the measurement of foci will be preferred to that of the micronuclei.

Thus, the TDNTBE is determined according to the formula:

$$TDNTBE=60/[0.4 \times NMN(t4)], \text{ if } NpH2AX(t0) \leq 3,$$

or according to the formula:

$$TDNTBE=60/[2+(0.4 \times NMN(t4))],$$

if NpH2AX(t0)>3.

On the basis of this quantitative analysis, a more qualitative diagnosis may then be made; it will be influenced by the quantitative analysis but will take into account any clinical elements brought to the awareness of the practitioner.

The correlation between the TDNTBE and the number of pH2AX foci and the number of micronuclei obtained after 24 hours of irradiation under 2 Gy, as a function of the number of pH2AX foci in the spontaneous state, was validated by the set of retrospective data collected on hyperradiosensitive irradiated patients with ATM gene mutation, who succumbed at 1 or 2 radiotherapy sessions in the 1970s. Cases of post-irradiation death (severity grade 5 according to the CTCAE classification) have been described in the literature since the 1970s until the present and systematically correspond either to cases of ataxia-telangiectasia or to the case of a patient with a ligase 4 mutation (see the article of A. Joubert et al., "DNA double-strand break repair defects in syndromes associated with acute radiation response: At least two different assays to predict intrinsic radiosensitivity?", published in the International Journal of Radiation Biology, vol. 84(2), p 107-125 (2008)). On the basis of these retrospective data, and knowing the total cumulative dose of these radiotherapy sessions, a parallel could be made with the corresponding number of non-repaired DSBs. In fact, the number of non-repaired double-strand breaks was measured in a large number of ataxic lines and in the single LIG4 mutation case (cell line 180BR). These lines systematically show a non-repaired break rate exceeding the lethality threshold after one dose. The values of the cell lines of AT and 180BR patients presented in table 2 contain proof of the determination of the threshold on the basis of which the number of non-repaired breaks is lethal for the patient. For these particular cases, the corresponding CTCAE grade is 5 (death). The TDNTBE can thus be defined as being the total cumulative dose enabling this number of non-repaired DSBs to be reached.

In another variant of the method according to the invention, the radiosensitivity group is first determined on said cell sample.

The definition of radiosensitivity groups (GROUP) helps the physician to determine, on the basis of scores according to the invention and the clinical picture of the patient, analogies with known genetic syndromes. These groups were defined in the publication of Joubert et al., which has already been cited.

According to the invention, it is considered that:
If NpH2AX(t4)<2 and
if NpATM(t1)>NpATM(t2) and
if NpATM(t1)>30 and
if A<10 and if B<5 and
if C<2
with the understanding that:
C=NpH2AX(t0)+NMN(t0);
B=% large nuclei (greater than 150 μm2 at t0;
A=NMRE11(t0)+number of small pH2AX foci per cell at t0;
then the radiosensitivity group (GROUP criterion) is considered to be "Group I": these cells are radioresistant.

If NpH2AX(t4)>8 or NMN(t4)>24)
then the radiosensitivity group (GROUP criterion) is considered to be "Group III": these cells are highly radiosensitive.

For all other conditions, it is considered that the GROUP criterion is "Group II": these cells show moderate radiosensitivity.

After having determined the radiosensitivity group of a patient, the TDNTBE according to one or the other of the variants presented above is then determined.

In practice, these formulas are particularly suitable for determining the TDNTBE of patients belonging to the radiosensitivity group of type II (moderate radiosensitivity), the radioresistant patients (group I) being capable of undergoing the standard treatment and the hyper-radiosensitive patients not being irradiated under any circumstances.

The invention is illustrated below with examples that do not limit the invention in any way. These examples relate to the analysis of cell lines of patients enabling the total dose not to be exceeded to be determined.

EXAMPLES

1. Preparation of the Test

A skin cell sample of a patient was taken by biopsy via the "skin punch biopsy" method known to a person skilled in the art. The cell sample was then placed in DMEM+20% sterile fetal bovine serum medium. The cell sample was then immediately transferred to a specialized laboratory so that the sample did not remain for longer than 38 hours at room temperature.

Upon receipt, the cell sample from the biopsy was established in the form of an amplifiable cell line according to a procedure well known to culture laboratories and a person skilled in the art: using in particular trypsin dispersion, the cells are again diluted in renewed medium and so on and so forth until the desired number of cells is obtained. After obtaining a sufficient number of cells (generally after one to three weeks), the first experiments were conducted using the method according to the invention. The cells were seeded on glass slides in Petri dishes. Some of these slides were irradiated on a medical irradiator according to a certified dosimetry with an absorbed dose D (2 Gy). Others were not irradiated; these represent the spontaneous state (absorbed dose 0 Gy).

The cells on glass slides were then fixed, lysed and hybridized. The cells were fixed in 3% paraformaldehyde and 2% sucrose for 15 minutes at room temperature and permeabilized in 20 mM of HEPES buffer solution (4-(2-hydroxyethyl)-1-piperazine ethane sulfonic acid) at pH 7.4, 50 mM NaCl, 3 mM $MgCl_2$, 300 mM sucrose, 0.5% Triton X-100 (a nonionic surfactant of formula t-Oct-$C_6H_4$—$(OCH_2CH_2)_x$OH with x=9-10, CAS No. 9002-93-1, supplied by Sigma Aldrich) for 3 minutes. Then, the cover slides were washed in phosphate-buffered saline (known as PBS) before immunological staining. The incubation took place for 40 minutes at 37° C. in PBS to which 2% bovine serum albumin (known as BSA or fraction V, supplied by Sigma Aldrich) was added, followed by a PBS washing. The primary anti-pH2AX antibodies were used at a concentration of 1:800, the other primary antibodies at 1:100. The incubations with secondary anti-mouse FITC or anti-rabbit TRITC antibodies (1:100, supplied by Sigma Aldrich) were performed at 37° C. in BSA at 2% for 20 minutes.

Glass slides were then treated with Vectashield™ containing DAPI (4,6-Diamidino-2-phenylindole) to mark the nucleus. The staining with DAPI also enables, indirectly, the determination of the number of cells in the quiescence G0/G1 phase (nuclei with homogeneous DAPI staining), in the synthesis S phase (nuclei with numerous pH2AX foci), in the quiescence $G_2$ phase (nuclei with heterogeneous DAPI staining) and in the mitosis M phase (visible chromosomes). The counter-staining with DAPI made it possible in particular to locate the nucleus in order to locate its cytoplasmic or nuclear location, and thus made it possible to quantify the micronuclei present.

The results were acquired from these slides on immunofluorescence microscope (Olympus model). The reading was performed directly by counting the foci obtained with different markers pH2AX, MRE11 and pATM on at least 50 cells in G0/G1 for each point and by dedicated image analysis software (image J).

2. Determination of the Number of pH2AX, MRE11 and pATM Foci in the Spontaneous State and after 10 Min (t1), 1 Hour (t2), 4 Hours (t3) and 24 Hours (t4) of Post-Irradiation Repair with an Absorbed Dose of 2 Gy, the Number of Micronuclei $N_{MN}(t)$ Observed in the Spontaneous State and after 24 Hours of Repair Time after Irradiation with an Absorbed Dose of 2 Gy for 100 Cells (in %), the Number of Small pH2AX Foci Per Cell in the Spontaneous State and the Percentage of Large Nuclei (Greater than 150 $\mu m^2$) at t0.

For the non-irradiated cells (spontaneous state, i.e. at t0), the mean number of mean number of pH2AX foci in the spontaneous state, the number of small pH2AX foci per cell in the spontaneous state, the percentage of large nuclei (greater than 150 $\mu m^2$) at t0 and the number of micronuclei observed spontaneously via the immunofluorescence analysis of these cells were acquired.

For the cells having undergone irradiation, the irradiation was performed with a medical accelerator that delivers 6 MV photons with an absorbed dose rate of 3 Gy $min^{-1}$. After irradiation with an absorbed dose of 2 Gy, the cells were preserved in the culture incubator at 37° C. For the irradiated cells (radiation-induced state), the samples were marked after a predetermined time lapse, namely: 10 minutes (t1), 1 hour (t2), 4 hours (t3) and 24 hours (t4) starting from the stop of irradiation, and the mean number of nuclear foci obtained with the pH2AX, MRE11 and pATM markers at these different post-irradiation repair times (10 min (t1), 1 hour (t2), 4 hours (t3) and 24 hours (t4)) were acquired. The number of micronuclei $N_{MN}(t)$ observed after 24 hours of repair time after irradiation with an absorbed dose of 2 Gy for 100 cells (in %) was also determined via analysis of the immunofluorescence of these samples.

To obtain results of statistical reliability sufficient to serve as a basis for a diagnosis, 3 independent series of irradiations were performed. The mean and standard error mean (SEM) of each of the numbers of foci in the spontaneous state (t0), after 10 min (t1), 1 hour (t2), 4 hours (t3) and 24 hours (t4)) of post-irradiation repair were calculated and some of the measurements are presented in the table below (cf. table 2), for different patient skin cell samples.

TABLE 2

Determination of the radiosensitivity of a patient and the TDNTBE as a function of the number of pH2AX, pATM and MRE11 foci in the spontaneous state (t0) and/or after 10 min (t1), 1 hour (t2), 4 hours (t3) and 24 hours (t4) of post-irradiation repair under 2 Gy, the number of micronuclei $N_{MN}(t)$ observed in the spontaneous state and after 24 hours of repair time after irradiation (t4) with an absorbed dose of 2 Gy for 100 cells (in %), the number of small pH2AX foci per cell in the spontaneous state and the percentage of large nuclei (greater than 150 µm²) at t0, for different patient skin cell samples (*this patient is radioresistant and may therefore undergo a standard radiotherapy protocol, i.e. receive 70 Gy for the treatment of prostate cancer, 40 Gy for the treatment of breast cancer).

| cell line | Number of spontaneous pH2AX foci (at t0) | Number of pH2AX foci per cell after 24 hours of repair (at t4) (%) | Mean number of radiation-induced micronuclei after 24 hours of repair (at t4) (%) | % of large nuclei (%) | number of small pH2AX foci at t0 | $N_{MRE11}$ (at t0) | Mean number of micronuclei (at t0) |
|---|---|---|---|---|---|---|---|
| HF19 | 0 ± 0 | 0.1 ± 0.0 | 1 ± 1 | 0 | 0 | 0 ± 0 | 0 ± 0 |
| 19HM | 0.65 ± 0.07 | 2.07 ± 0.16 | 4.67 ± 1.15 | 0 | 0 | 0 ± 0 | 4.67 ± 1.15 |
| 29CLB | 1.45 ± 0.23 | 1.9 ± 0.34 | 10.67 ± 1.15 | 0 | 43.33 | 0.3 ± 0.3 | 4.33 ± 0.58 |
| 01DAX | 1.38 ± 0.24 | 4.66 ± 0.79 | 10.17 ± 6.37 | 0 | 0 | 0 ± 0 | 10.17 ± 6.37 |
| 13CLB | 0.69 ± 0.1 | 1.25 ± 0.21 | 8.33 ± 3.11 | 0 | 0 | 0 ± 0 | 3 ± 1 |
| 35CLB | 1.09 ± 0.23 | 2.01 ± 0.15 | 9.67 ± 2 | 33 | 0 | 0 ± 0 | 2 ± 0 |
| 01PAU | 2.45 ± 1.21 | 1.65 ± 0.13 | 5.33 ± 1.15 | 1.67 | 43.33 | 0 ± 0 | 5.33 ± 1.15 |
| AT2EM | 4.00 ± 1.00 | 16.00 ± 4.00 | 25.00 ± 3.00 | 5 | 100 | 0 ± 0 | 25.0 ± 3.0 |
| AT5BI | 3.00 ± 1.00 | 17.00 ± 6.00 | 30.00 ± 3.00 | 5 | 100 | 0 ± 0 | 30 ± 3 |
| AT4BI | 2.00 ± 1.00 | 22.00 ± 4.00 | 39.00 ± 3.00 | 5 | 100 | 0 ± 0 | 4 ± 1 |
| AT1BR | 2.00 ± 1.00 | 12.00 ± 4.00 | 28.00 ± 3.00 | 5 | 100 | 0 ± 0 | 4.2 ± 1.0 |
| 180BR | 3.00 ± 1.00 | 35.00 ± 3.00 | 37.00 ± 3.00 | 5 | 100 | 0 ± 0 | 4.5 ± 2.0 |

| cell line | $N_{pATM}$ after 10 minutes of repair (at t2) | $N_{pATM}$ after 1 hour of repair (at t2) | radiosensitivity of the sample determined according to the invention | Severity grade | Total dose not to be exceeded in skin equivalent (Gy) 1st variant taking into account pH2AX foci | 2nd variant taking into account micronuclei |
|---|---|---|---|---|---|---|
| HF19 | 40 ± 2 | 20 ± 1 | group I | 1 | 600* | 75 |
| 19HM | 26 ± 4 | 16.7 ± 8.8 | group II | 2 | 27-31 | 26-43 |
| 29CLB | 20 ± 6 | 23.3 ± 3.3 | group II | 3 | 27-38 | 13-16 |
| 01DAX | 16.7 ± 6.7 | 23.3 ± 8.8 | group II | 3 | 11-16 | 9-39 |
| 13CLB | 13.3 ± 3.3 | 15 ± 3 | group II | 4 | 41-58 | 13-29 |
| 35CLB | 30 ± 6 | 16.7 ± 3.3 | group II | 2 | 28-32 | 13-20 |
| 01PAU | 0 ± 0 | 23.3 ± 4.4 | group II | 3 | 34-39 | 23-36 |
| AT2EM | 0 ± 0 | 1 ± 0 | group III | 5 | 2-4 | 5-6 |
| AT5BI | 0 ± 0 | 0 ± 0 | group III | 5 | 2-5 | 4-5 |
| AT4BI | 0 ± 0 | 3 ± 1 | group III | 5 | 2-3 | 4 |
| AT1BR | 0 ± 0 | 1 ± 0 | group III | 5 | 4-8 | 5-6 |
| 180BR | 36 ± 2 | 20 ± 1 | group III | 1-2 | 3-4 | |

2.3 Predictive Evaluation of the Total Dose not to be Exceeded

Thus, for different patient skin cell samples (cf. table 2), the total dose not to be exceeded for a patient who will undergo or who is undergoing radiotherapy in order to avoid a potentially lethal reaction (TDNTBE) was determined.

The total dose not to be exceeded (TDNTBE), expressed in Gray (Gy), was determined by the following formulas:

TDNTBE=60/NpH2AX(t4) if NpH2AX(t0)>3, or

TDNTBE=60/[NpH2AX(t4)+NpH2AX(t0)] if NpH2AX(t0)>3.

According to another variant of the invention, the total dose not to be exceeded (TDNTBE), expressed in Gray (Gy) was also determined by the following formulas, taking into account the mean number of micronuclei observed at time t for 100 cells [in %]:

TDNTBE=60/[0.4×NMN(t4)], if NpH2AX(t0)≤3, or according to the formula:

TDNTBE=60/[2+(0.4×NMN(t4))], if NpH2AX(t0)>3.

The times t0 and t4 correspond respectively to the spontaneous state, i.e. non-irradiated and to time t4 after irradiation with an absorbed dose D.

The quantitative values of the total dose not to be exceeded (TDNTBE), expressed in Gray (Gy) are indicated in table 2.

The severity grades 2 to 4 concern tissue reactions (for example: dermatitis, proctitis, etc.). Severity grade 1 concerns manageable adverse effects, which are often confused according to practitioners with grade 0 (no effect).

What is claimed is:

1. A method to personalize a radiation dose for a subject in need thereof, the method comprising:
   predicting cellular sensitivity of a cell sample to ionizing radiation, said cell sample obtained from cells sampled from the subject in a non-irradiated or slightly-irradiated area, including:
      amplifying said cells sampled to form the cell sample;
      determining on said cell sample a mean number $N_{pH2AX}(t)$ of nuclear foci obtained with a pH2AX marker at an observation time t and/or a mean number $N_{MN}(t)$ of nuclear foci observed at time t for 100 cells [in %], said observation time t being a time t=0 min (t0, non-irradiated state), and observation times t1, t2, t3, and/or t4 after irradiation with an absorbed dose D;
      determining a total dose not to be exceeded (TDNTBE), expressed in Gray (Gy), as a value from a first calculation that is a function of $N_{pH2AX}(t4)$ and/or $N_{MN}(t4)$ to be used based on when a value from a second calculation as a function of $N_{pH2AX}(t0)$ satisfies a predetermined threshold, wherein t4 is a fixed value that represents a time for which a DNA break level reaches its residual value and which is around 24 hours, t3 is a fixed value that represents a time after which around 25% of double-strand breaks (DSBs) are repaired in cells from radioresistant subjects and which is between 3 times t2 and 5 times t2 or around 4 hours, t2 is a fixed value that represents a time after which around 50% of the DSBs are repaired in cells from radioresistant subjects and which is between 5 times t1 and 7 times t1 or around 60 minutes, and t1 is a fixed value that represents a time after which a number of recognized DSBs reaches its maximum in cells from radioresistant subjects and which is around 10 minutes, and wherein when $N_{pH2AX}(t0)>3$ the first calculation is TDNTBE=60/[$N_{pH2AX}(t4)+N_{pH2AX}(t0)$], and when $N_{pH2AX}(t0) \leq 3$ the first calculation is TDNTBE=60/$N_{pH2AX}(t4)$; and
   providing the TDNTBE to limit administration of the radiation dose to the TDNTBE or to avoid the administration of the radiation dose to the subject.

2. The method of claim 1, wherein the value of the second calculation is further as a function of $N_{MN}(t0)$.

3. The method of claim 1, wherein said sampled cells are fibroblast cells obtained from a skin biopsy of the subject.

4. The method of claim 1, wherein the absorbed dose D is 2 Gy.

5. The method of claim 1, wherein:
   t1 is between 8 minutes and 12 minutes;
   t2 is between 50 minutes and 70 minutes;
   t3 is between 3.5 hours and 4.5 hours; and
   t4 is between 22 hours and 26 hours.

6. The method of claim 5, wherein:
   t1 is 10 minutes;
   t2 is 60 minutes;
   t3 is 4 hours;
   t4 is 24 hours; and
   the absorbed dose D is 2 Gy.

7. The method of claim 1, wherein the determination at least of $N_{pH2AX}(t)$ involves an immunofluorescence test.

8. The method of claim 1, wherein cells obtained from radioresistant subjects are cells showing an in vitro clonogenic survival rate greater than 55% after irradiation with an absorbed dose of 2 Gy.

9. The method of claim 1, wherein cells obtained from radioresistant subjects are cells sampled from one or more subjects not having shown significant tissue reactions during or after a radiotherapy treatment.

10. The method of claim 1, wherein a mean number of nuclear foci obtained with the pH2AX marker at observation time t1, t2, and t3 is used to verify a shape of a kinetic curve of DSB site recognition.

11. The method of claim 1, further including determining a mean number of nuclear foci obtained with a pATM marker $N_{pATM}(t)$ and/or a MRE11 marker $N_{MRE11}(t)$ at observation time t.

12. The method of claim 11, further including determining that the sample is considered to be radioresistant (group I) if $N_{pH2AX}(t4)<2$ and $N_{pATM}(t1)>N_{pATM}(t2)$ and $N_{pATM}(t1)>30$ and A<10 and B<5 and C<2, wherein C=$N_{pH2AX}(t0)+N_{MN}(t0)$ B=% large nuclei (greater than 150 µm$^2$) at t0 and A=$N_{MRE11}(t0)$+Number of small pH2AX foci per cell at t0.

13. The method of claim 12, further including determining that the sample is considered to be hyper-radiosensitive (group III) if $N_{pH2AX}(t4)>8$ or $N_{MN}(t4)>24$.

14. The method of claim 13, further including determining that the sample is considered to be moderately radiosensitive (group II) for all other conditions.

15. The method of claim 1, further comprising determining a radiosensitivity group of the subject before determining the TDNTBE.

* * * * *